(12) United States Patent
Seck Mor

(10) Patent No.: US 8,141,553 B2
(45) Date of Patent: Mar. 27, 2012

(54) CONDOM APPLICATOR DEVICE

(76) Inventor: Maty Seck Mor, Yaounde (CM)

( * ) Notice: Subject to any disclaimer, the term of this patent is extended or adjusted under 35 U.S.C. 154(b) by 464 days.

(21) Appl. No.: 12/507,024

(22) Filed: Jul. 21, 2009

(65) Prior Publication Data

US 2010/0012131 A1     Jan. 21, 2010

Related U.S. Application Data

(63) Continuation-in-part of application No. 12/296,094, filed on Oct. 3, 2008, now abandoned.

(51) Int. Cl.
*A61F 6/04* (2006.01)
*A61F 6/02* (2006.01)

(52) U.S. Cl. ........................ 128/844; 128/842

(58) Field of Classification Search ................ 128/842, 128/844, 917, 918; 604/317, 346; 223/112, 223/11; 24/30.5 S, 30.15, 15
See application file for complete search history.

(56) References Cited

U.S. PATENT DOCUMENTS

| | | | |
|---|---|---|---|
| 4,875,491 A | 10/1989 | Parrone | |
| 5,471,998 A | 12/1995 | Kuyumciyan | |
| 5,549,120 A | 8/1996 | Persson et al. | |
| 5,549,196 A | 8/1996 | Kassman | |
| D459,469 S | 6/2002 | Johnson | |
| 6,425,397 B1 | 7/2002 | Liehs | |
| 6,732,736 B2 * | 5/2004 | Sanchez | 128/844 |
| 6,918,392 B2 | 7/2005 | Kassman | |

FOREIGN PATENT DOCUMENTS

| WO | 2005079714 A1 | 9/2005 |
|---|---|---|
| WO | 2006025755 A1 | 3/2006 |
| WO | 2008016316 A1 | 2/2008 |

\* cited by examiner

*Primary Examiner* — Patricia Bianco
*Assistant Examiner* — Ophelia Hawthorne

(57) ABSTRACT

A condom applicator for mounting a condom comprising a first concentric ring having a generally flat outer and inner surface; a second concentric ring positioned outside of the first concentric ring having a generally flat outer and inner surface; a panel connecting both first side edges of the first and second concentric rings; a first notch and a second notch disposed in the second concentric ring for allowing the second concentric ring to be rolled inside out; a third notch and a fourth notch disposed in the first concentric ring for allowing the first concentric ring to be pulled inside out; and a first bump disposed on the inner surface of the second concentric ring or on the outer surface of the first concentric ring for narrowing the space between the first and second concentric ring to help the condom temporarily stay mounted to the condom applicator.

17 Claims, 6 Drawing Sheets

CONDOM APPLICATOR DEVICE

CROSS REFERENCE

This application is a continuation-in-part and claims benefit to the non-provisional patent application Ser. No. 12/296,094 filed Oct. 3, 2008 now abandoned, PCT patent application Ser. No. PCT/OA2007/000001 filed Apr. 4, 2007, and African Intellectual Property Organization patent application serial number 1200600116 filed Apr. 5, 2006 the disclosures of which are incorporated in their entirety herein by reference.

FIELD OF THE INVENTION

The present invention is directed to a device for assisting the application of a condom.

BACKGROUND OF THE INVENTION

Condoms are known to be very effective at preventing sexually transmitted infections. Some individual may find applying a condom difficult. The present invention features a novel device for applying a condom.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
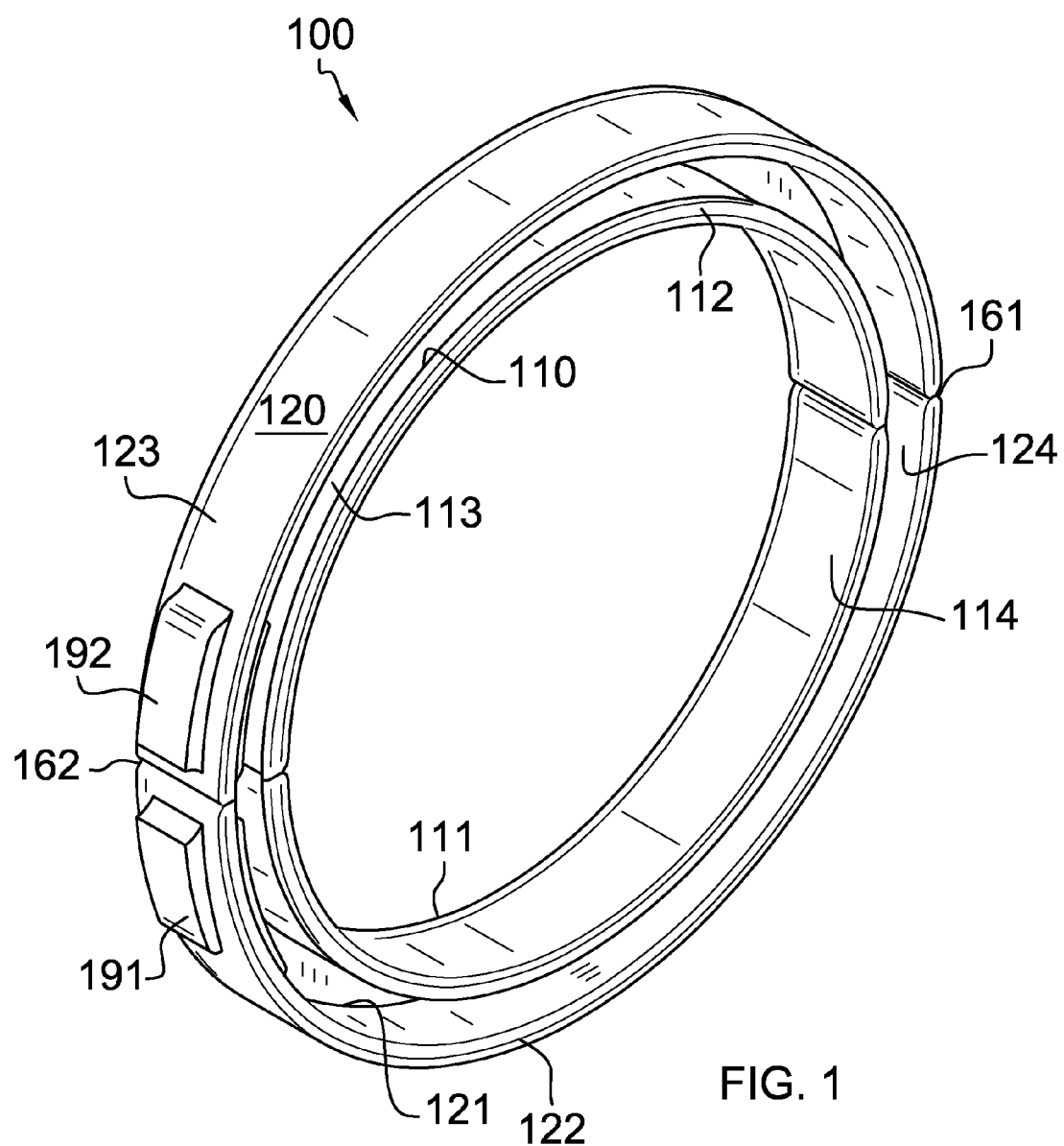
FIG. 1 is a perspective view of a condom applicator device of the present invention.
Figure 2:
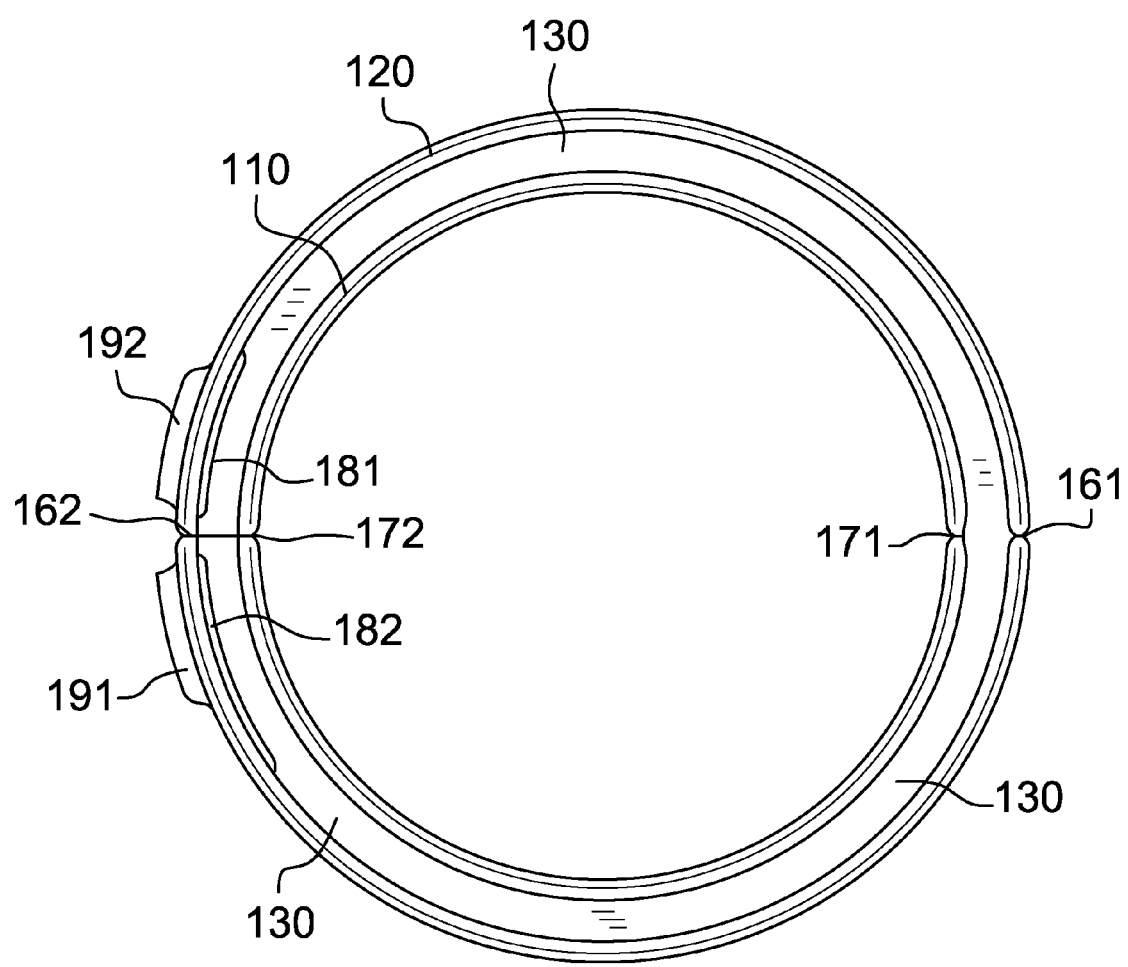
FIG. 2 is a bottom view of the condom applicator device of FIG. 1.
Figure 3:
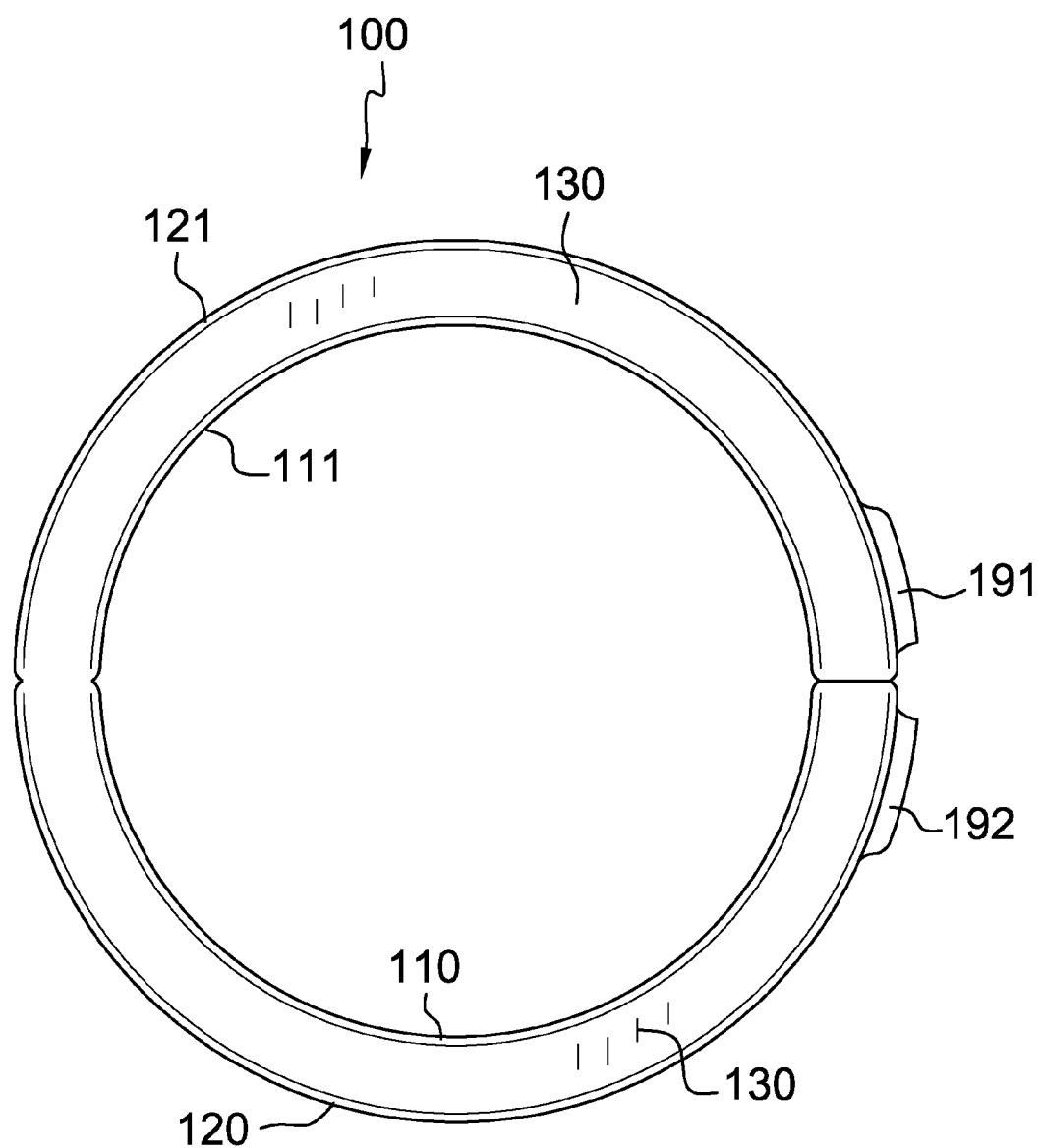
FIG. 3 is a top view of the condom applicator device of FIG. 1.
Figure 4:
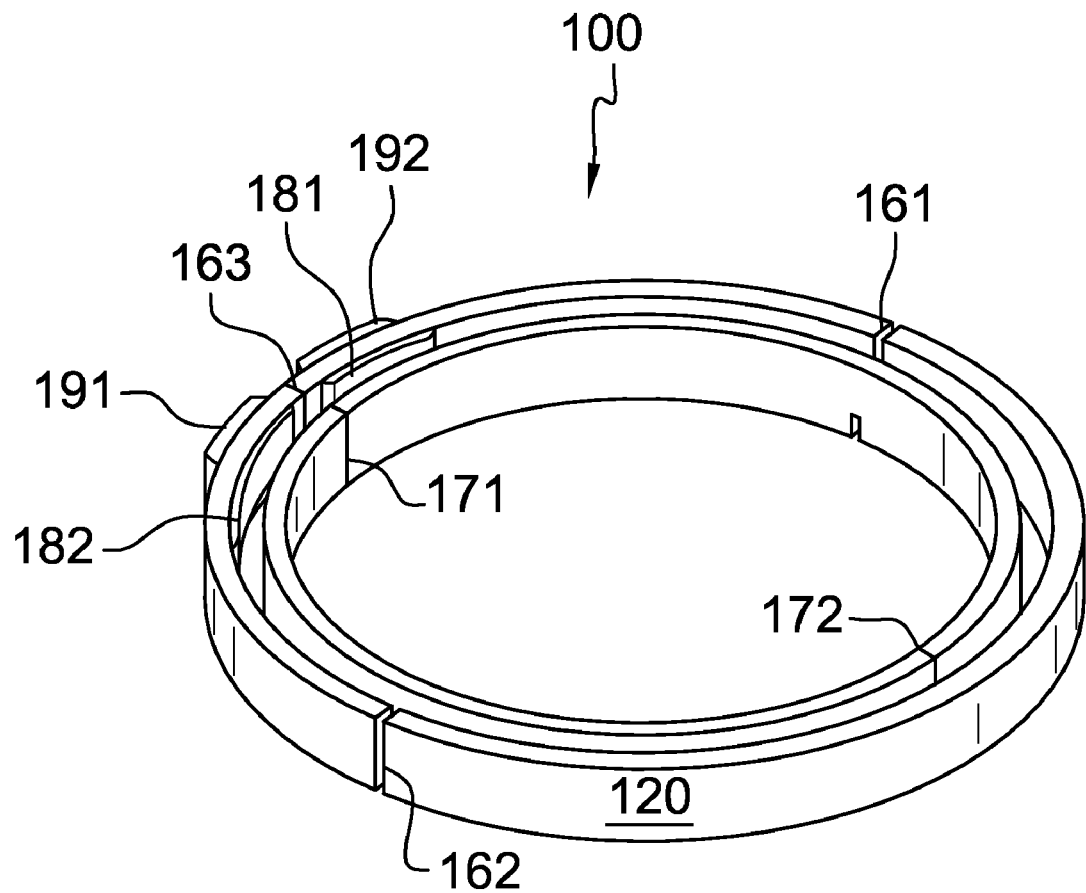
FIG. 4 is a perspective view of a condom applicator device of the present invention.
Figure 5:
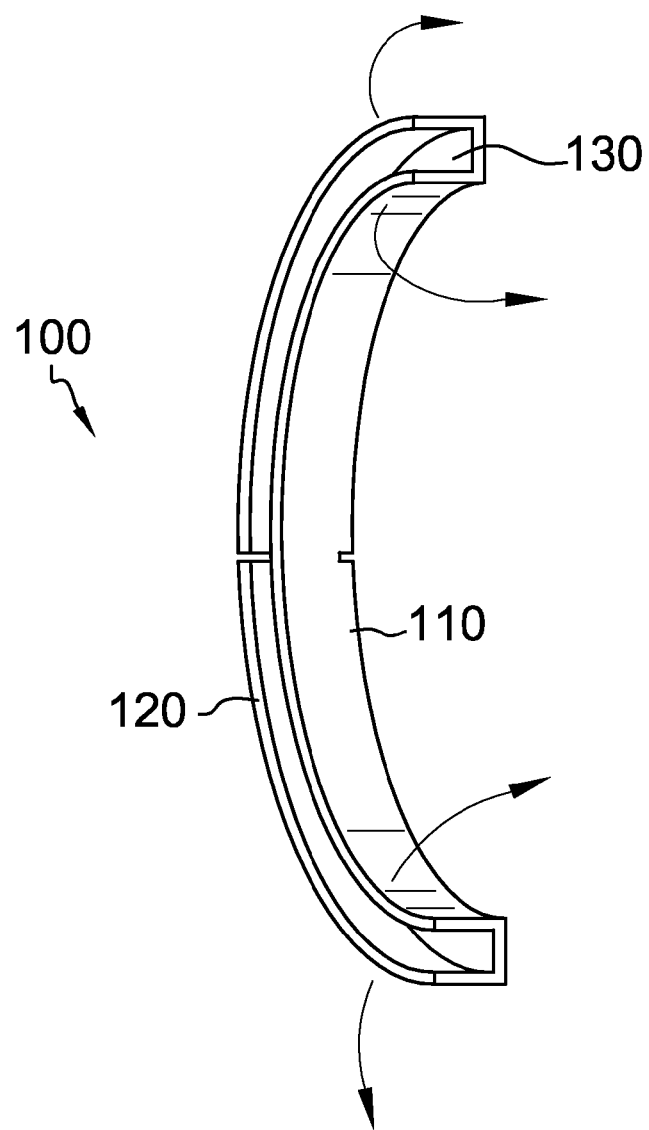
FIG. 5 is a cross sectional view of the condom applicator device of FIG. 4.
Figure 6:
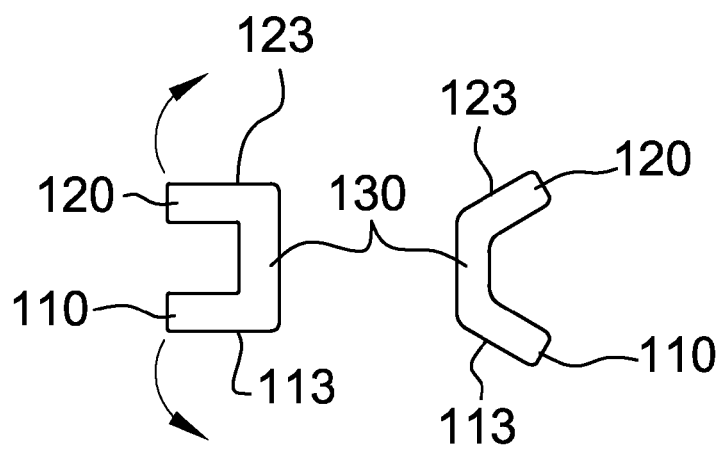
FIG. 6 is a cross sectional view of the condom applicator device of the present invention, wherein the device is turned inside out.
Figure 7:
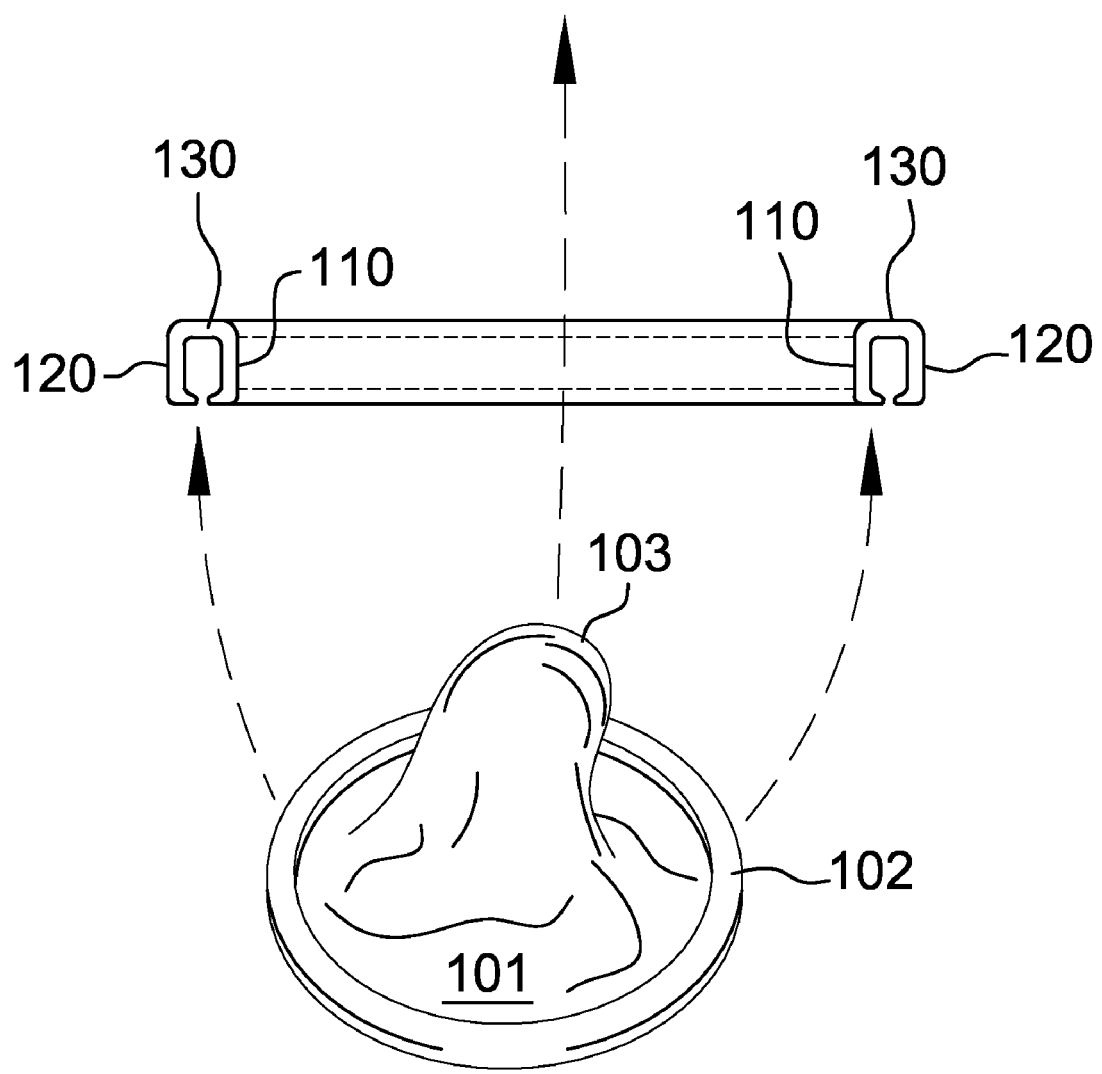
FIG. 7 is a cross sectional view of the condom applicator device of the present invention and a perspective view of a condom.

Referring now to FIG. 1-7, the present invention features a condom applicator 100. The condom applicator device 100 comprises a first concentric ring 110 having a first side edge 111, a second side edge 112, a generally flat outer surface 113, and a generally flat inner surface 14. Outside of the first concentric ring 110 (and aligned with the first concentric ring 110) is a second concentric ring 120. The second concentric ring 120 has a first side edge 121, a second side edge 122, a generally flat outer surface 123, and a generally flat inner surface 124.

The first concentric ring 110 is attached to the second concentric ring 120 via a ring-shaped panel 130 that extends from the first side edge 111 of the first concentric ring 110 to the first side edge 121 of the second concentric ring 120. In some embodiments, the panel 130 covers the entire space between the first side edge 111 the first concentric ring 110 to the first side edge 121 of the second concentric ring 120 (e.g., the panel 130 is ring-shaped). In some embodiments, the panel 130 covers a portion of the space between the first side edge 111 of the first concentric ring 110 to the first side edge 121 of the second concentric ring 120.

The first concentric ring 110, second concentric ring 120, and panel 130 are constructed from a soft, flexible material. The flexible material allows a user to squeeze the condom applicator device 100, for example the user can press on opposing sides of the outer surface 123 of the second concentric ring 120, which changes the circular shape of the device to be more oval. The squeezing of the device 100 may be necessary in order for the condom 101 to be properly mounted on the device 100 (or for easier removal). The flexible soft material may also help prevent the condom 101 from being damaged during the application process.

Disposed in the second concentric ring 120 are a first notch 161 and a second notch 162. The notches are important for allowing the second concentric ring 120 to be pulled inside out. For example, the second side edge 122 of the second concentric ring 120 can be folded outwardly and rolled (pulled) back in the direction of the panel 130, causing the inner surface 124 of the second concentric ring 120 to be exposed (see FIG. 6). The second concentric ring 120 may have more than two notches disposed therein (e.g., an additional notch 163). In some embodiments, the first notch 161 is opposite the second notch 162 (see FIG. 2). In some embodiments, the additional notch 163 is disposed in around halfway between the first notch 161 and the second notch 162.

Disposed in the first concentric ring 110 are a third notch 171 and a fourth notch 172. The notches allow for the first concentric ring 110 to be pulled (rolled) inside out. For example, the second side edge 112 of the first concentric ring 110 can be pulled inwardly (e.g., toward the center point of the circle formed by the first concentric ring 110) such that the inner surface 113 is exposed (see FIG. 6). In some embodiment, the first concentric ring 110 has more than two notches. In some embodiments, the third notch 171 is opposite the fourth notch 172.

To mount a condom 101 on the device 100 of the present invention, the rolled portion 102 of the condom 101 is fit it in between the first concentric ring 110 and second concentric ring 120. The top 103 of the condom 101 is gently pushed though the center of the first concentric ring 110 (e.g., in the direction of the panel 130) (see FIG. 7). The outer surface of the condom 101 (e.g., near the top 103) should be in contact with the inner surface 114 of the first concentric ring 110. A user can then insert his penis into the condom (e.g., into the top end 103 of the condom). The panel 130 of the condom applicator device 100 is positioned/oriented to be facing upwardly toward the top end of the penis and the rolled portion of the condom 101 is positioned oriented to be facing downwardly toward the pelvic area. The condom applicator 100 (e.g., the panel 130) can then be gently pushed downwardly to slide the device 100 towards the user's pelvic area. As the device 100 is slid downwardly, the condom 101 is unrolled onto the user's penis.

In some embodiments, a first bump 181 is disposed on the inner surface 124 of the second concentric ring 120 (or outer surface 113 of the first concentric ring 110). The first bump 181 narrows the space between the first concentric ring 110 and the second concentric ring 120, which makes the rolled portion of the condom fit snugly and securely when mounted.

This may help the condom stay mounted to the device 100. In some embodiments, a second bump 182 is disposed on the inner surface 124 of the second concentric ring 120 (or outer surface 113 of the first concentric ring 110). In some embodiments, the first bump 181 and second bump 182 are near a notch (e.g., the first notch 161, the second notch 162). In some embodiments, the first bump 181 and second bump 182 are on opposite sides of the notch. The first bump 181 and second bump 182 may be elongated, for example stretch from the notch along the inner surface 124 of the second concentric ring 120. Without wishing to limit the present invention to any theory or mechanism, it is believed that an elongated first bump 181 and/or an elongated second bump 182 is advantageous because it may help the condom be easily placed and/or may help the condom stay secured to the device when in use. This may be advantageous, for example, if the condom is placed upside down.

In some embodiments, a first thumb tab 191 is disposed on the outer surface 123 of the second concentric ring 120. The first thumb tab 191 may help a user grip the device 100 more easily and/or securely. In some embodiments, a second thumb tab 192 is disposed on the outer surface 123 of the second concentric ring 120. In some embodiments, the thumb tabs are on opposing sides of a notch (e.g., the first notch 161, the second notch 162).

When the condom 101 has been applied, the device 100 may be removed while leaving the condom 101 in place. A user can turn the device 100 inside out, for example the second concentric ring 120 can be folded outwardly causing the inner surface 124 the second concentric ring 120 to be exposed and the first concentric ring 110 can be pulled inwardly such that the inner surface 113 is exposed. In some embodiments, the panel 130 is torn when the device 100 is turned inside out for removal. For example, a portion of the panel 130 at a notch may tear (see the second notch 162 and the fourth notch 172 in FIG. 2). The tearing of the panel opens the concentric rings, allowing the device 100 to be easily taken off after application of the condom 101.

Various modifications of the invention, in addition to those describe herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A condom applicator for mounting a condom, said condom applicator comprising:
   (a) a first concentric ring having a generally flat outer surface and a generally flat inner surface;
   (b) a second concentric ring positioned outside of the first concentric ring, the second concentric ring having a generally flat outer surface and a generally flat inner surface;
   (c) a panel connecting a first side edge of the first concentric ring to a first side edge of the second concentric ring;
   (d) a first notch and a second notch disposed in the second concentric ring for allowing the second concentric ring to be rolled inside out;
   (e) a third notch and a fourth notch disposed in the first concentric ring for allowing the first concentric ring to be pulled inside out; and
   (f) a first bump disposed on the inner surface of the second concentric ring or on the outer surface of the first concentric ring, the first bump narrows space between the first concentric ring and the second concentric ring to help the condom temporarily stay mounted to the condom applicator when in use.

2. The condom applicator of claim 1 further comprising a first thumb tab disposed on the outer surface of the second concentric ring.

3. The condom applicator of claim 2 further comprising a second thumb tab disposed on the outer surface of the second concentric ring.

4. The condom applicator of claim 3, wherein the first thumb tab and the second thumb tab are on opposing sides of the first notch or the second notch.

5. The condom applicator of claim 1, wherein the first bump is positioned near the first notch, the second notch, the third notch, or the fourth notch.

6. The condom applicator of claim 5, wherein the first bump and the second bump are on opposite sides of the first notch, the second notch, the third notch, or the fourth notch.

7. The condom applicator of claim 1, wherein the first notch is opposite the second notch.

8. The condom applicator of claim 1, wherein the second concentric ring has more than two notches disposed therein.

9. The condom applicator of claim 1, wherein the third notch is opposite the fourth notch.

10. The condom applicator of claim 1, wherein the first concentric ring has more than two notches disposed therein.

11. The condom applicator of claim 1 further comprising a second bump disposed on the inner surface of the second concentric ring or on outer surface of the first concentric ring.

12. The condom applicator of claim 1, wherein the first concentric ring and/or the second concentric ring and/or the panel are constructed from a soft and flexible material.

13. A method of applying a condom, said method comprising:
   (a) obtaining a condom applicator comprising:
      (i) a first concentric ring having a generally flat outer surface and a generally flat inner surface;
      (ii) a second concentric ring positioned outside of the first concentric ring, the second concentric ring having a generally flat outer surface and a generally flat inner surface;
      (iii) a panel connecting a first side edge of the first concentric ring to a first side edge of the second concentric ring;
      (iv) a first notch and a second notch disposed in the second concentric ring for allowing the second concentric ring to be rolled inside out;
      (v) a third notch and a fourth notch disposed in the first concentric ring for allowing the first concentric ring to be pulled inside out; and
      (vi) a first bump disposed on the inner surface of the second concentric ring or on the outer surface of the first concentric ring, the first bump narrows space between the first concentric ring and the second concentric ring to help the condom temporarily stay mounted to the condom applicator when in use;
   (b) inserting a rolled portion of the condom snugly in between the first concentric ring and second concentric ring;
   (x) pushing a top end of the condom gently though the first concentric ring such that an outer surface of the condom contacts the inner surface of the first concentric ring;

(x) placing the top end of the condom over a top end of a penis of a user, wherein the panel of the condom applicator is oriented upwardly facing the top end of the penis and the rolled portion of the condom is oriented downwardly facing a pelvic area of the user;

(x) pushing on the panel of the condom applicator downwardly toward the pelvic area of the user whereby the condom is unrolled onto the penis of the user.

14. The method of claim 13, wherein the condom applicator can be removed by turning the condom applicator inside out.

15. The method of claim 14, wherein as the condom applicator is turned inside out the panel is torn allowing the condom applicator to be removed.

16. The method of claim 13 further comprising squeezing opposing sides of the outer surface of the second concentric ring to help insert the rolled portion of the condom in between the first concentric ring and the second concentric ring.

17. The method of claim 13, wherein the condom applicator can be removed while leaving the condom in place.

* * * * *